United States Patent
Grell et al.

(10) Patent No.: US 8,180,092 B2
(45) Date of Patent: May 15, 2012

(54) CONVERTER SYSTEM FOR AN ACTIVE NOISE COMPENSATION APPARATUS

(75) Inventors: Axel Grell, Burgdorf (DE); André Grandt, Wedemark (DE)

(73) Assignee: Sennheiser electronic GmbH & Co. KG, Wedemark (DE)

( * ) Notice: Subject to any disclaimer, the term of this patent is extended or adjusted under 35 U.S.C. 154(b) by 901 days.

(21) Appl. No.: 12/084,518

(22) PCT Filed: Nov. 1, 2006

(86) PCT No.: PCT/EP2006/010491
§ 371 (c)(1),
(2), (4) Date: Aug. 26, 2008

(87) PCT Pub. No.: WO2007/051606
PCT Pub. Date: May 10, 2007

(65) Prior Publication Data
US 2009/0136055 A1    May 28, 2009

(30) Foreign Application Priority Data
Nov. 2, 2005   (DE) .................. 10 2005 052 548

(51) Int. Cl.
*H04R 3/00*    (2006.01)
*H04R 25/00*   (2006.01)

(52) U.S. Cl. ......... 381/371; 381/370; 381/372; 381/122

(58) Field of Classification Search .................. None
See application file for complete search history.

(56) References Cited

U.S. PATENT DOCUMENTS

| 5,182,774 A | 1/1993 | Bourk |
| 5,809,156 A * | 9/1998 | Bartels et al. .................. 381/370 |
| 7,499,555 B1 * | 3/2009 | Isvan ............................ 381/71.6 |

FOREIGN PATENT DOCUMENTS

| DE | 1 876 054 | 7/1963 |
| DE | 36 16 563 | 12/1987 |
| EP | 0 737 022 | 10/1996 |
| EP | 0 967 592 | 12/1999 |
| JP | 51-4328 | 6/1949 |
| JP | 61-81286 | 5/1986 |
| JP | 5-36991 | 5/1993 |
| JP | 2005072703 | 3/2005 |
| WO | 01/56330 | 8/2001 |

* cited by examiner

*Primary Examiner* — Anh Mai
(74) *Attorney, Agent, or Firm* — Frommer Lawrence & Haug LLP

(57) ABSTRACT

There is provided a transducer system for an active noise compensation apparatus, which has a first end at the ear side and an electroacoustic transducer. The electroacoustic transducer has a diaphragm system and a magnet system, wherein the central region of the diaphragm system is curved towards the magnet system and is in the form of an inverted calotte. A sensor microphone is arranged in a volume between the first end and the region of the curvature of the diaphragm system.

2 Claims, 1 Drawing Sheet

CONVERTER SYSTEM FOR AN ACTIVE NOISE COMPENSATION APPARATUS

CROSS-REFERENCE TO RELATED APPLICATIONS

This is a national phase application of International Application No. PCT/EP2006/010491, filed Nov. 1, 2006, which claims priority of German Application No. 10 2005 052 548.2, filed Nov. 2, 2005, the complete disclosures of which are hereby incorporated by reference.

BACKGROUND OF THE INVENTION a) Field of the Invention

The present invention concerns an electroacoustic transducer system for an active noise compensation apparatus and a headset having such a transducer system.

b) Description of the Related Art

Conventional active noise compensation apparatuses have a reproduction transducer system with a sensor microphone which is arranged between the electroacoustic transducer and the ear of a wearer, in particular as closely as possible to the ear of the wearer. The sound recorded by the sensor microphone is used for active noise compensation.

DE 1 876 054 discloses a diaphragm for an electroacoustic transducer, wherein a portion of the diaphragm is curved in a cup shape.

U.S. Pat. No. 5,182,774 discloses a headset with an active noise compensation apparatus. In that case a sensor microphone is arranged between a transducer system and an ear of a wearer so that the microphone projects mechanically and there can be a certain risk of injury.

OBJECT AND SUMMARY OF THE INVENTION

Therefore the primary object of the present invention is to provide a transducer system and/or an active noise compensation apparatus which has a reduced risk of injury.

That object is attained by a transducer system for an active noise compensation apparatus comprising a first end at the ear side, an electroacoustic reproduction transducer which has a diaphragm system and a magnet system, wherein a central region of the diaphragm system is curved towards the magnet system and is in the form of an inverted calotte, and a sensor microphone for recording interference noise arranged in a volume between the first end and the region of the curvature of the diaphragm system.

The object is also attained by a headset comprising a transducer system as described above and/or an active noise compensation apparatus comprising a transducer system as described above.

There is thus provided a transducer system for an active noise compensation apparatus, which has a first end at the ear side and an electroacoustic reproduction transducer. The electroacoustic transducer has a diaphragm system and a magnet system, wherein the central region of the diaphragm system is curved towards the magnet system and is in the form of an inverted calotte. A sensor microphone is arranged in the region of the curvature of the diaphragm system.

The invention concerns a transducer system for an active noise compensation apparatus, wherein an (electro)acoustic transducer has an inverted calotte and the sensor microphone as viewed from the ear is arranged in front of the electroacoustic transducer or the diaphragm system, that is to say the sensor microphone is arranged axially spaced in relation to the diaphragm system. That has in particular the advantage that the structural height of an active noise compensation apparatus is decreased and a risk of injury is reduced. The sensor microphone is thus arranged in the region between the inverted calotte and an ear of a wearer. Such an arrangement means that the sensor microphone can be disposed very close to the ear of a wearer. That is particularly advantageous for active noise compensation. In that case the cup of the acoustic transducer is of such a configuration that it is curved towards the (axially spaced) magnet system. Thus the sensor microphone can be placed within the free volume which is afforded by the arrangement of the inverted calotte, afforded by the inward curvature of the diaphragm.

The invention is described in greater detail hereinafter with reference to the accompanying drawing.

DESCRIPTION OF THE PREFERRED EMBODIMENTS

Figure 1:
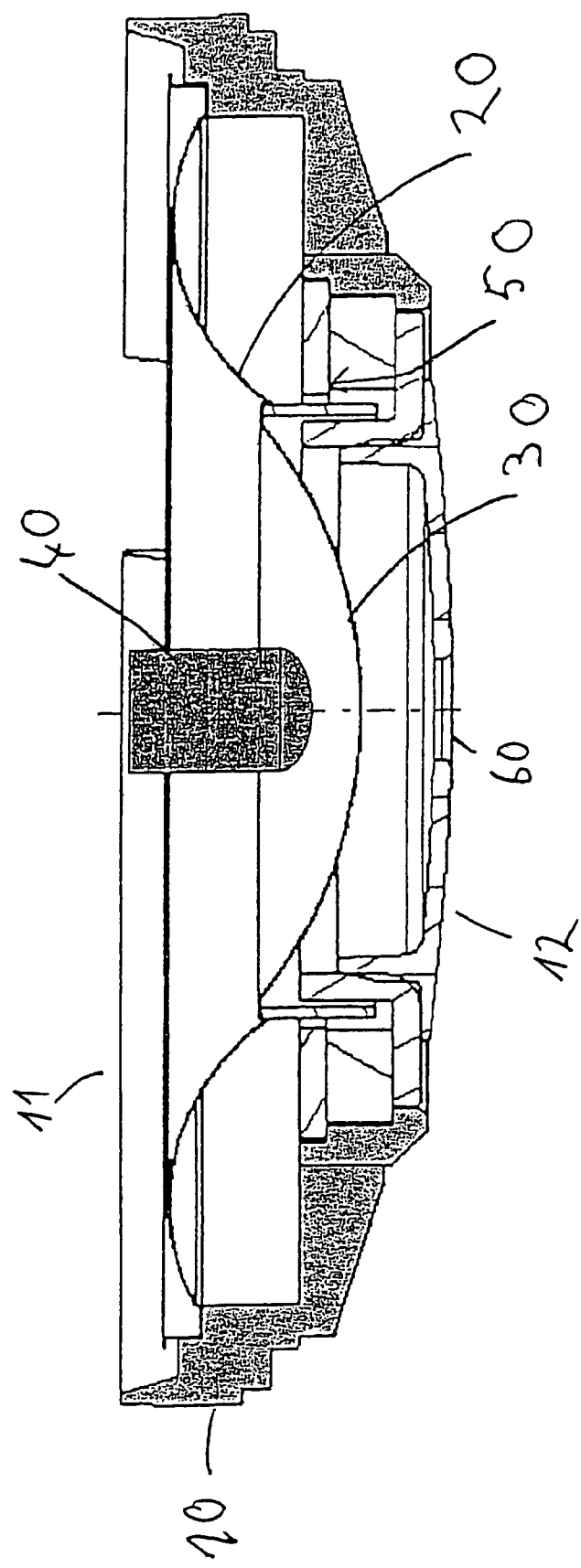
FIG. 1 shows a diagrammatic view in section of an electroacoustic reproduction transducer according to the invention.

FIG. 1 shows a diagrammatic view in section of an electroacoustic transducer system. Shown here is in particular an electroacoustic reproduction transducer 10 for the reproduction of audio signals, which can be used for example in an active noise compensation apparatus. The electroacoustic transducer 10 has a first end at the ear side, and a second end 12 remote from the ear, as well as a diaphragm system 20 with an inverted calotte 30. Provided in the free volume which is afforded by the inward curvature of the diaphragm system by virtue of the arrangement of the inverted calotte 30 (that is to say in the volume between the inverted calotte 30 and the first end 11 or the ear of the wearer) is a sensor microphone 40 for recording noise or sound, which is required for active noise sound compensation. The transducer 10 also has a magnet system 50 and an opening 60, remote from an ear, in the second end 12.

An active noise compensation apparatus is disclosed in patent specification EP 0 737 022 B1, the disclosure of which is referred to for the purposes of disclosure of the invention. In particular the disclosure of the principle of the active noise compensation apparatus, as described with reference to FIGS. 1 through 3 and in paragraphs [0019] through [0028], with the reproduction transducer and the sensor microphone, is referred to for the purposes of disclosure. The compensation circuit is shown in FIG. 3 and described in paragraph [0028], which is also referred to for the purposes of disclosure.

The holes or openings 60 in the second end remote from the ear serve to provide that the air in the volume between the inverted calotte 30 and the housing 10 can escape outwardly. Preferably the spacing between the sensor microphone 40 and the inverted calotte 30 should be as small as possible without the microphone 10 and the inverted calotte 30 colliding at maximum deflection. A spacing which is as small as possible between the sensor microphone 40 and the inverted calotte 30 provides that the transit time is reduced so that the 180° phase shift of the recorded sound, which is required for active noise compensation, can be better achieved. The reproduction transducer serves to reproduce the noise-compensated audio signal, in which respect noise compensation is effected as described in EP 0 737 022 B1, FIG. 3, paragraph [0028], on the basis of the noise or sound recorded by the sensor microphone.

Thus the sensor microphone 40 is arranged directly in front of the inverted calotte 30. In that respect the sensor microphone 40 is preferably held by a resonator (not shown).

The arrangement described with reference to FIG. 1 of the inverted calotte 30 and the sensor microphone 40 provides that the transmission distance between the electroacoustic transducer 10 and the sensor microphone or measuring microphone 40 for active noise sound compensation can be considerably reduced.

Although FIG. 1 shows an orientation of the sensor microphone 40, that is substantially perpendicular to an ear, the sensor microphone can also be arranged at any other angle.

The magnet system 50 is preferably arranged on the outside as shown in FIG. 1 so that the inverted calotte 30 has space therebetween. As an alternative thereto the magnet system can also be arranged inwardly. In such a case however the magnets are preferably shaped to correspond to the curvature of the inverted calotte 30. The shaping of the magnet system can be used for acoustic dimensioning.

While the foregoing description and drawings represent the present invention, it will be obvious to those skilled in the art that various changes may be made therein without departing from the true spirit and scope of the present invention.

What is claimed is:

1. A headphone comprising:
   an active noise compensation means having:
      an electroacoustic reproduction transducer; and
      a sensor microphone for recording interference noise;
   wherein the electroacoustic reproduction transducer comprises:
      a first end;
      a diaphragm; and
      a magnet system;
      wherein a central region of the diaphragm is curved towards the magnet system, and is in the form of an inverted cup; and
   wherein the sensor microphone is arranged in a volume between the first end and the region of the inverted cup of the diaphragm system, and extends towards the region of the inverted cup.

2. A headset comprising:
   an active noise compensation means having:
      an electroacoustic reproduction transducer; and
      a sensor microphone for recording interference noise;
   wherein the electroacoustic reproduction transducer comprises:
      a first end;
      a diaphragm; and
      a magnet system;
      wherein a central region of the diaphragm is curved towards the magnet system, and is in the form of an inverted cup; and
   wherein the sensor microphone is arranged in a volume between the first end and the region of the inverted cup of the diaphragm system, and extends towards the region of the inverted cup.

* * * * *